United States Patent
Holdsworth et al.

(10) Patent No.: US 10,180,483 B2
(45) Date of Patent: Jan. 15, 2019

(54) 3D PRINTED PHYSICAL PHANTOM UTILIZED IN MEASURING 3D GEOMETRIC DISTORTION OCCURRING IN MRI AND CT IMAGES

(71) Applicants: David W Holdsworth, London (CA); Matthew G. Teeter, London (CA); Jacques S. Milner, London (CA); Steven I. Pollmann, London (CA); Maria Drangova, London (CA)

(72) Inventors: David W Holdsworth, London (CA); Matthew G. Teeter, London (CA); Jacques S. Milner, London (CA); Steven I. Pollmann, London (CA); Maria Drangova, London (CA)

(*) Notice: Subject to any disclaimer, the term of this patent is extended or adjusted under 35 U.S.C. 154(b) by 911 days.

(21) Appl. No.: 14/694,220

(22) Filed: Apr. 23, 2015

(65) Prior Publication Data

US 2015/0309149 A1    Oct. 29, 2015

Related U.S. Application Data

(60) Provisional application No. 61/984,032, filed on Apr. 24, 2014.

(51) Int. Cl.
    *G01R 33/58* (2006.01)
    *G01R 33/565* (2006.01)
    (Continued)

(52) U.S. Cl.
    CPC ............. *G01R 33/58* (2013.01); *A61B 6/032* (2013.01); *A61B 6/466* (2013.01); *A61B 6/583* (2013.01);
    (Continued)

(58) Field of Classification Search
    USPC ................... 324/300–322; 600/407–435; 382/128–133
    See application file for complete search history.

(56) References Cited

U.S. PATENT DOCUMENTS

| | | |
|---|---|---|
| 4,644,276 A | 2/1987 | Sierocuk et al. |
| 5,005,578 A | 4/1991 | Greer et al. |

(Continued)

OTHER PUBLICATIONS

J.F. Aubry, J. Cheung, O. Morin, L. Beaulieu, I.C. Hsu, J. Pouliot. Investigation of geometric distortions on magnetic resonance and cone beam computed tomography images used for planning and verification of high-dose rate brachytherapy cervical cancer treatment. Brachytherapy. 9, 266-273 (2010).

(Continued)

*Primary Examiner* — Melissa Koval
*Assistant Examiner* — Tiffany Fetzner
(74) *Attorney, Agent, or Firm* — Brunet & Co. Ltd.; Robert A. H. Brunet; Hans Koenig

(57) ABSTRACT

3D printing in MRI-compatible plastic resin has been used to fabricate and implement a geometric distortion phantom for MRI and CT imaging. The sparse grid structure provides a rigid and accurate phantom with identifiable intersections that are larger than the supporting members, which produces images that are amenable to fully automated quantitative analysis using morphometric erosion, greyscale segmentation and centroiding. This approach produces a 3D vector map of geometric distortion that is useful in clinical applications where geometric accuracy is important, either in routine quality assurance or as a component of distortion correction utilities.

20 Claims, 13 Drawing Sheets

(51) Int. Cl.
*A61B 6/03* (2006.01)
*A61B 6/00* (2006.01)
*G01R 33/56* (2006.01)

(52) U.S. Cl.
CPC .............. *A61B 6/52* (2013.01); *G01R 33/565* (2013.01); *G01R 33/5608* (2013.01)

(56) References Cited

U.S. PATENT DOCUMENTS

| | | | |
|---|---|---|---|
| 5,872,829 A | 2/1999 | Wischmann et al. | |
| 6,591,004 B1* | 7/2003 | VanEssen | G06T 17/00 128/922 |
| 7,330,026 B2 | 2/2008 | Wang et al. | |
| 7,535,227 B1 | 5/2009 | Koch et al. | |
| 7,664,298 B2* | 2/2010 | Lang | A61B 6/469 382/128 |
| 7,907,766 B2* | 3/2011 | Lehel | A61B 5/02007 378/4 |
| 7,995,822 B2* | 8/2011 | Lang | A61B 6/469 382/128 |
| 8,031,919 B2* | 10/2011 | Eskildsen | G06K 9/48 128/922 |
| 8,189,889 B2 | 5/2012 | Pearlstein et al. | |
| 8,260,018 B2* | 9/2012 | Lang | A61B 6/469 382/128 |
| 8,577,115 B2* | 11/2013 | Gering | G06T 7/174 382/132 |
| 8,781,191 B2* | 7/2014 | Lang | A61B 6/469 382/128 |
| 8,781,197 B2* | 7/2014 | Wang | G01R 33/54 382/131 |
| 9,092,691 B1* | 7/2015 | Beaumont | G06T 7/0014 |
| 9,155,501 B2* | 10/2015 | Lang | A61B 6/469 |
| 9,299,156 B2* | 3/2016 | Zalis | G06F 19/321 |
| 2005/0010106 A1* | 1/2005 | Lang | A61B 6/469 600/425 |
| 2007/0092864 A1* | 4/2007 | Reinhardt | G06T 7/0012 435/4 |
| 2008/0159610 A1* | 7/2008 | Haas | A61B 5/02007 382/131 |
| 2008/0170791 A1* | 7/2008 | Eskildsen | G06K 9/48 382/199 |
| 2009/0169083 A1 | 7/2009 | Li | |
| 2009/0226060 A1* | 9/2009 | Gering | G06T 7/11 382/128 |
| 2009/0304248 A1* | 12/2009 | Zalis | G06F 19/321 382/131 |
| 2010/0130832 A1* | 5/2010 | Lang | A61B 6/469 600/300 |
| 2011/0044524 A1* | 2/2011 | Wang | G01R 33/54 382/131 |
| 2012/0027283 A1* | 2/2012 | Lang | A61B 6/469 382/132 |
| 2012/0201438 A1 | 8/2012 | Vermandel et al. | |
| 2013/0039592 A1* | 2/2013 | Lang | A61B 6/469 382/232 |
| 2015/0003712 A1* | 1/2015 | Lang | A61B 6/469 382/132 |
| 2015/0145515 A1* | 5/2015 | Liu | G01R 33/243 324/309 |
| 2015/0254850 A1* | 9/2015 | Jorgensen | G06T 7/0016 382/133 |
| 2015/0309149 A1* | 10/2015 | Holdsworth | G01R 33/58 324/309 |
| 2016/0253797 A1* | 9/2016 | Lang | A61B 6/469 382/132 |
| 2018/0038922 A1* | 2/2018 | Lu | G01R 33/5601 |

OTHER PUBLICATIONS

L.N. Baldwin, K. Wachowicz, B.G. Fallone. A two-step scheme for distortion rectification of magnetic resonance images. Med Phys. 36, 3917-3926 (2009).

L.N. Baldwin, K. Wachowicz, S.D. Thomas, R. Rivest, B.G. Fallone. Characterization, prediction, and correction of geometric distortion in 3 T MR images. Med Phys. 34, 388-399 (2007).

Z. Chen, C.M. Ma, K. Paskalev, J. Li, J. Yang, T. Richardson, L. Palacio, X. Xu, L. Chen. Investigation of MR image distortion for radiotherapy treatment planning of prostate cancer. Phys Med Biol. 51, 1393-1403 (2006).

S.P. Crijns, C.J. Bakker, P.R. Seevinck, H. de Leeuw, J.J. Lagendijk, B.W. Raaymakers. Towards inherently distortion-free MR images for image-guided radiotherapy on an MRI accelerator. Phys Med Biol. 57, 1349-1358 (2012).

S.J. Doran, L. Charles-Edwards, S.A. Reinsberg, M.O. Leach. A complete distortion correction for MR images: I. Gradient warp correction. Phys Med Biol. 50, 1343-1361 (2005).

S. Kiryu, Y. Inoue, Y. Masutani, T. Haishi, K. Yoshikawa, M. Watanabe, K. Ohtomo. Distortion correction in whole-body imaging of live mice using a 1-Tesla compact magnetic resonance imaging system. Jpn J Radiol. 29, 353-360 (2011).

D. Kittle, B. Holshouser, J.M. Slater, B.D. Guenther, N.P. Pitsianis, R.D. Pearlstein. Technical note: rapid prototyping of 3D grid arrays for image guided therapy quality assurance. Med Phys. 35, 5708-5712 (2008).

S.P. Krishnan, et al. A review of rapid prototyped surgical guides for patient-specific total knee replacement. J Bone Joint Surg Br. 94(11), 1457-1461 (2012).

B.H. Kristensen, F.J. Laursen, V. Logager, P.F. Geertsen, A. Krarup-Hansen. Dosimetric and geometric evaluation of an open low-field magnetic resonance simulator for radiotherapy treatment planning of brain tumours. Radiother Oncol. 87, 100-109 (2008).

N. Maikusa, F. Yamashita, K. Tanaka, O. Abe, A. Kawaguchi, H. Kabasawa, S. Chiba, A. Kasahara, N. Kobayashi, T. Yuasa, N. Sato, H. Matsuda, T. Iwatsubo. Improved volumetric measurement of brain structure with a distortion correction procedure using an ADNI phantom. Med Phys. 40, 062303 (2013).

T. Mizowaki, Y. Nagata, K. Okajima, M. Kokubo, Y. Negoro, N. Araki, M. Hiraoka. Reproducibility of geometric distortion in magnetic resonance imaging based on phantom studies. Radiother Oncol. 57, 237-242 (2000).

J.G. Och, G.D. Clarke, W.T. Sobol, C.W. Rosen, S.K. Mun. Acceptance testing of magnetic resonance imaging systems: report of AAPM Nuclear Magnetic Resonance Task Group No. 6. Med Phys. 19, 217-229 (1992).

Y. Pauchard, M.R. Smith, M.P. Mintchev. Improving geometric accuracy in the presence of susceptibility difference artifacts produced by metallic implants in magnetic resonance imaging. IEEE Trans Med Imaging. 24, 1387-1399 (2005).

R.R. Price, L. Axel, T. Morgan, R. Newman, W. Perman, N. Schneiders, M. Selikson, M. Wood, S.R. Thomas. Quality assurance methods and phantoms for magnetic resonance imaging: report of AAPM nuclear magnetic resonance Task Group No. 1. Med Phys. 17, 287-295 (1990).

E. Schneider and M. Nessaiver, The Osteoarthritis Initiative (OAI) magnetic resonance imaging quality assurance update. Osteoarthritis Cartilage. 21(1), 110-116 (2013).

T. Stanescu, H.S. Jans, K. Wachowicz, B.G. Fallone. Investigation of a 3D system distortion correction method for MR images. J Appl Clin Med Phys. 11, 2961 (2010).

T. Stanescu, K. Wachowicz, D.A. Jaffray. Characterization of tissue magnetic susceptibility-induced distortions for MRIgRT. Med Phys. 39, 7185-7193 (2012).

S.F. Tanner, D.J. Finnigan, V.S. Khoo, P. Mayles, D.P. Dearnaley, M.O. Leach. Radiotherapy planning of the pelvis using distortion corrected MR images: the removal of system distortions. Phys Med Biol. 45, 2117-2132 (2000).

R. Viard, N. Betrouni, M. Vermandel, S. Mordon, J. Rousseau, M. Vanhoutte. Characterization and 3D correction of geometric distortion in low-field open-magnet MRI. Conf Proc IEEE Eng Med Biol Soc. 2008, 3649-3652 (2008).

(56) References Cited

OTHER PUBLICATIONS

D. Wang and D.M. Doddrell. A proposed scheme for comprehensive characterization of the measured geometric distortion in magnetic resonance imaging using a three-dimensional phantom. Med Phys. 31, 2212-2218 (2004a).

D. Wang, D.M. Doddrell, G. Cowin. A novel phantom and method for comprehensive 3-dimensional measurement and correction of geometric distortion in magnetic resonance imaging. Magn Reson Imaging. 22, 529-542 (2004b).

D. Wang, W. Strugnell, G. Cowin, D.M. Doddrell, R. Slaughter. Geometric distortion in clinical MRI systems Part II: correction using a 3D phantom. Magn Reson Imaging. 22, 1223-1232 (2004).

D. Wang, W. Strugnell, G. Cowin, D.M. Doddrell, R. Slaughter. Geometric distortion in clinical MRI systems Part I: evaluation using a 3D phantom. Magn Reson Imaging. 22, 1211-1221 (2004).

\* cited by examiner

Component 1: *design and construct a phantom with known geometric property (ground truth)* step 1.1: design an unique 3D shape, which is comprised of spheres supported by smaller cylindrical struts at known spacing;

step 1.2: fabricate accurate plastic structure of the designed 3D shape;

step 1.3: evaluate for geometric accuracy using a measuring microscope or a micro-CT scanner;

step 1.4: immerse the structure in a liquid within a plastic container.

Fig. 1a

Component 2: *image the phantom using MR or CT scanner*

| step 2.1: locate the phantom at the isocenter of a MR or CT scanner; |

| step 2.2: image the phantom by using a 3D spin-echo pulse sequence (MRI) or high-resolution CT acquisition sequence; |

| step 2.3: reconstruct the 3D image of the phantom. |

Component 3: *generate a distortion vector map from ground truth and the MR images* step 3.1: perform signal-intensity inhomogeneity correction in the axial and trans-axial directions of the MR images;

step 3.2: interpolate the resulting images to a finer isotropic resolution;

step 3.3: segment the interpolated images based on a grey-scale threshold;

step 3.4: erode the segmented (binary) image to remove the struts and retain the spheres;

step 3.5: identify and centroid the spheres in the eroded images to create a 3D point cloud of control points;

step 3.6: generate a vector map, which adjusts the observed grid to a best-fit with the known grid location.

Fig. 1c

3D PRINTED PHYSICAL PHANTOM UTILIZED IN MEASURING 3D GEOMETRIC DISTORTION OCCURRING IN MRI AND CT IMAGES

CROSS-REFERENCE TO RELATED APPLICATIONS

This application claims the benefit of U.S. Provisional Patent Application Ser. No. 61/984,032 filed Apr. 24, 2014, the entire contents of which is herein incorporated by reference.

FIELD

This application relates to methods and apparatuses relayed to imaging, particularly to methods and apparatuses for measuring 3D distortions in images.

BACKGROUND

The capability for routine and accurate characterization—and correction—of geometric distortion is becoming increasingly important for MRI applications in image-guided therapy. Applications where accurate geometrical measurements from MRI images are required include image-guided radiotherapy (Crijns 2012; Aubry 2010; Chen 2006), quantitative brain imaging (Maikusa 2013), and quantification during imaging for osteoarthritis (Schneider 2013) and the preparation of patient-specific positioning guides (Krishnan 2012). In order to correct for inherent geometric distortion, a variety of fiducial grids and sheets have been proposed, typically based on regularly structured 3D grids (Baldwin 2007; Wang 2004a; Wang 2004b; Kiryu 2011; Mizowaki 2000; Stanescu 2010; Stanescu 2012), rods (Doran 2005; Tanner 2000), or 3D distributions of glass marker beads (Viard 2008). Grid phantoms based on commercially fabricated polystyrene grids suffer from manufacturing imprecision and difficulty in post-processing and analysis to determine line intersections. Glass marker beads placed in custom-fabricated trays are complicated to fabricate.

Thus, there is still a need for dimensionally accurate 3D grid phantoms that are able to be imaged using MRI or CT techniques, are readily processable using automated techniques to determine grid intersections, and are simple to manufacture.

SUMMARY

Recent advances in additive manufacturing—or "3D printing"—have made it possible to create accurate plastic structures of any desired 3D shape, facilitating an entirely new design of geometric distortion phantom. 3D printing techniques have been used to design and fabricate a 3D grid phantom, comprised of beads supported by cylindrical struts at known spacing. When immersed in a fluid, such as a paramagnetic liquid, the phantom can be used to obtain images that facilitate automated segmentation and analysis of the 3D distortion field within an image.

In one embodiment, a method is provided for measuring geometric distortions of a 3D medical imaging system, the method comprising: providing a 3D phantom comprising a plurality of control points, each having a pre-determined location; obtaining a 3D image of the phantom (using either magnetic resonance imaging or computed tomography); identifying, preferably automatically, the control points in the image by segmentation and morphological erosion; determining the location of the control points in the image; comparing the location of the control points in the image with the pre-determined location of the control points in the phantom; and, deriving a spatial vector, preferably a 3D vector map, that quantifies the geometric discrepancy between the control points in the image and the pre-determined location of the control points in the phantom.

The 3D phantom may comprise control points having a shape that is differentiable in an image from structure of the phantom used to support the control points. For example, the control points may have a size that is larger than that of the supporting structure for the control points. The control points may have a shape that is different from the shape of the supporting structure. The control points may be spherical and the supporting structure may be cylindrical. The spherical control points may have a diameter that is larger than a diameter of the cylindrical supporting structure.

The 3D phantom may be manufactured using additive manufacturing (3D printing). The additive manufacturing may comprise photopolymeric printing, for example using a rigid plastic resin that is cured by UV light. The 3D phantom may comprise rigid supporting structure. The 3D phantom may comprise rigid control points. The 3D phantom may comprise control points that are integrally formed with the supporting structure. The 3D phantom may be fabricated using a material that is compatible with both MRI and CT imaging. The 3D phantom may be fabricated from a material that is resistant to swelling when immersed in a particular fluid, for example a paramagnetic liquid.

The plurality of control points may be located in a pre-specified and known distribution in space relative to a known reference point of the phantom, with either uniform or non-uniform spacing relative to the reference point. The control points may be defined from clusters that have dimensions exceeding the dimensions of the elongate struts that support them in their pre-determined locations.

The control points may not be distributed contiguously across the entire three-dimensional volume of the phantom, and the phantom may include, for example, cavities and openings that facilitate conformal geometric measurements in proximity around magnetically active objects, such as orthopedic implants.

In another embodiment a system is provided for measuring geometric distortion errors in a medical imaging system, comprising a three-dimensional calibration phantom comprising a plurality of control points connected to each other by supporting structure, the phantom suitable for imaging by the medical imaging system, and a computer provided with machine executable instructions configured to execute an analysis program that determines the centroids of the control points in three-dimensional space from an image of the phantom acquired using the medical imaging system and compares these centroids to the true locations of the control points and calculates a spatial vector that relates each centroid to its true location.

The 3D phantom may be provided within a leak-tight transparent container that surrounds the phantom containing a fluid comprising, for example, a paramagnetic liquid (for MRI applications) or air (for CT applications).

In another embodiment, there is provided a computer provided with machine executable instructions configured to apply a specified correction for axial and radial intensity non-uniformity across the imaging volume.

The location of the control points in the image may be obtained by segmenting the boundary of the three-dimensional phantoms from the image, based on, for example, operator-specified global grey-scale threshold values, and subsequently performing morphological erosion of the three-dimensional binary image volume with a specified number of boundary surface elements (voxels) removed, until the support structure that connects the control points is removed, leaving isolated clusters of volume elements at known locations in the image. The method may further comprise deriving the accurate (i.e. sub-voxel) location of the centroid of each control-point cluster in three-dimensional space, and comparing those locations with the known true locations of the control points in the phantom.

Further features will be described or will become apparent in the course of the following detailed description. It should be understood that each feature described herein may be utilized in any combination with any one or more of the other described features, and that each feature does not necessarily rely on the presence of another feature except where evident to one of skill in the art.

BRIEF DESCRIPTION OF THE DRAWINGS

For clearer understanding, preferred embodiments will now be described in detail by way of example, with reference to the accompanying drawings, in which:

FIG. 1a is flowchart showing the first component of the system and method of FIG. 1;

FIG. 1c is a flowchart showing the third component of the system and method of FIG. 1;

DETAILED DESCRIPTION

Figure 1:
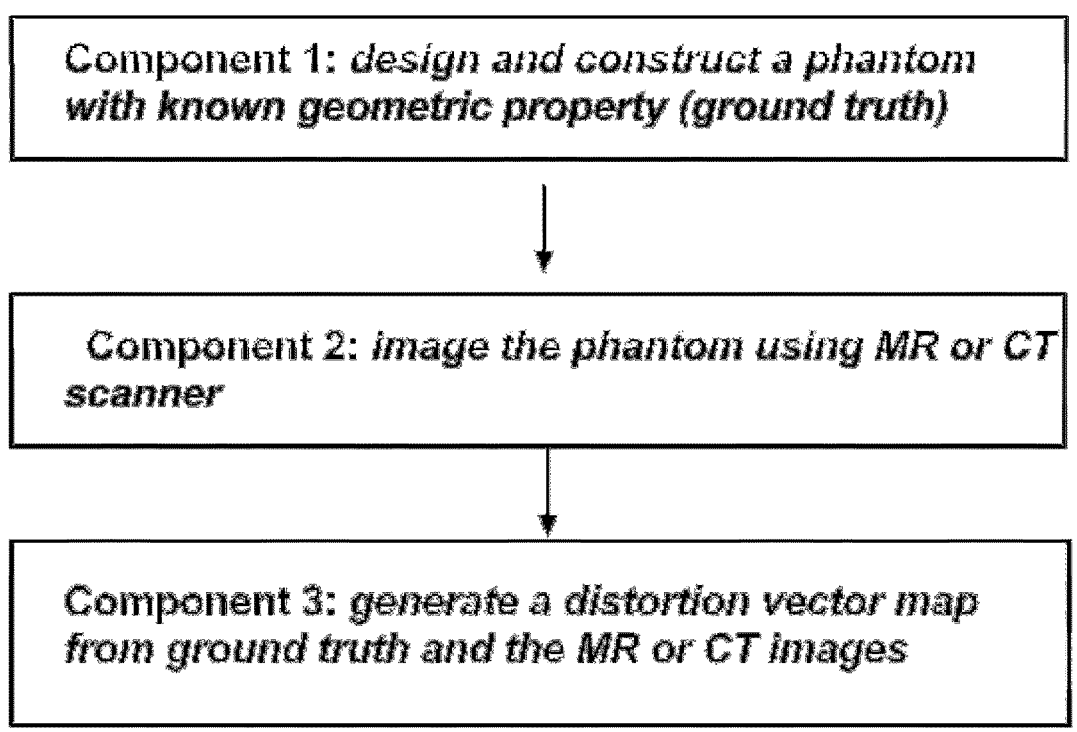
FIG. 1 summarizes the three components of the system and method.

Referring to FIG. 1, a system and method is generally shown comprising three main components. Referring to FIG. 1a, in step 1.1 a 3D phantom is created comprising a plurality of control points arranged in space in a pre-determined location. The control points are differentiable from supporting structure on the basis of size. In one embodiment, the control points have a larger size than the supporting structure used to position the control points in their pre-determined locations. This allows the control points to be readily differentiated from the support structure. The control points may comprise spheres having a larger diameter than the elongate members of the support structure, which may be cylindrical in shape. The design of the location of the control points takes into account features of the object desired to be imaged and their magnetic or density characteristics; for example, if an orthopedic implant, such as a metallic prosthesis is desired to be imaged, the phantom may be designed with a cavity conforming in shape to an exterior of the implant, thereby allowing a precise calibration to be obtained for control points on the exterior of the implant.

Referring to step 1.2, once the phantom is designed, the phantom is fabricated. Although a number of techniques can be used for fabrication, it is desirable that the phantom retain sufficient structural strength and rigidity that the control points do not move from within pre-specified tolerance of their pre-determined design location. Movement of the points from their design location introduces error into the calibration and is thus undesirable. Accordingly, it has been found that forming the control points integrally with the supporting structure provides a desired degree of robustness, structural strength and rigidity to the phantom as compared with assembling the phantom from interconnecting pieces. A technique that has been found amenable to this type of fabrication is additive manufacturing, commonly referred to as 3D printing.

A variety of additive manufacturing techniques are commercially available; however, since it is desired that the phantom be formed from a plastic resin, a preferred technique is photopolymeric printing using UV light as a curative. A plastic resin is chosen that is discernable from surrounding fluid (paramagnetic liquid or air, depending on whether MRI or CT imaging techniques are used), provides sufficient structural strength, and does not swell or otherwise dimensionally distort upon absorption of the surrounding fluid. Suitable examples include acrylic and/or polyacrylate resins.

Referring to step 1.3, following fabrication the phantom is measured for geometric accuracy relative to the design and the precise location of the control points with reference to a particular datum (e.g. a center of the phantom) is determined. This measurement may be obtained using a co-ordinate measuring machine, a measuring microscope, a micro CT scanner, or any other suitably accurate technique.

Referring to step 1.4, the phantom is then optionally immersed within a fluid tight transparent container, such as a plastic container. The container provides a protective shell for the phantom and also controls the magnetic and density properties of the space surrounding the phantom in order to provide consistent contrast between the phantom and the surrounding space.

Figure 1B:
FIG. 1b is a flowchart showing the second component of the system and method of FIG. 1.
Figure 1B:

Referring to FIG. 1b, step 2.1, the phantom is imaged using a three dimensional MRI or CT scanner. The phantom is first located at an isocenter of the MRI or CT scanner so that the spatial vectors obtained through analysis of the image can be used to calibrate the MRI or CT machine relative to a known registration reference of the machine. Then, referring to step 2.2, an image is obtained using either a 3D spin-echo pulse sequence (for MRI) or a high resolution CT sequence. This is then used in step 2.3 to reconstruct a precise image of the phantom that is registered to the isocenter of the scanner.

Referring to FIG. 1c, in step 3.1, the signal intensity is corrected for inhomogeneity relative to the isocenter in both the axial and trans-axial directions. This improves the uniformity of contrast between the phantom and the surrounding space across the entire image, which simplifies subsequent image processing. Referring to steps 3.2 and 3.3, the images are first interpolated to a finer isotropic resolution and then segmented based on a grey-scale threshold to obtain crisp image boundaries. Referring to step 3.4, the crisp boundaries of the segmented image are eroded on a pixel by pixel basis to obtain new image boundaries. The effect of this erosion technique on the image is similar to what would be obtained if the phantom were dipped in acid for a known amount of time and then re-imaged; in other words, all boundaries of the image are reduced in size in 3D space by the same increment. By performing successive erosion operations, the supporting structure eventually disappears from the image, leaving behind clusters of pixels representative of the control points. Thus, the control points can be readily discerned from the supporting structure on the basis of size. Referring to step 3.5, a centroid of each cluster of pixels is identified to determine a precise location for each control point represented in the image.

Figure 10:
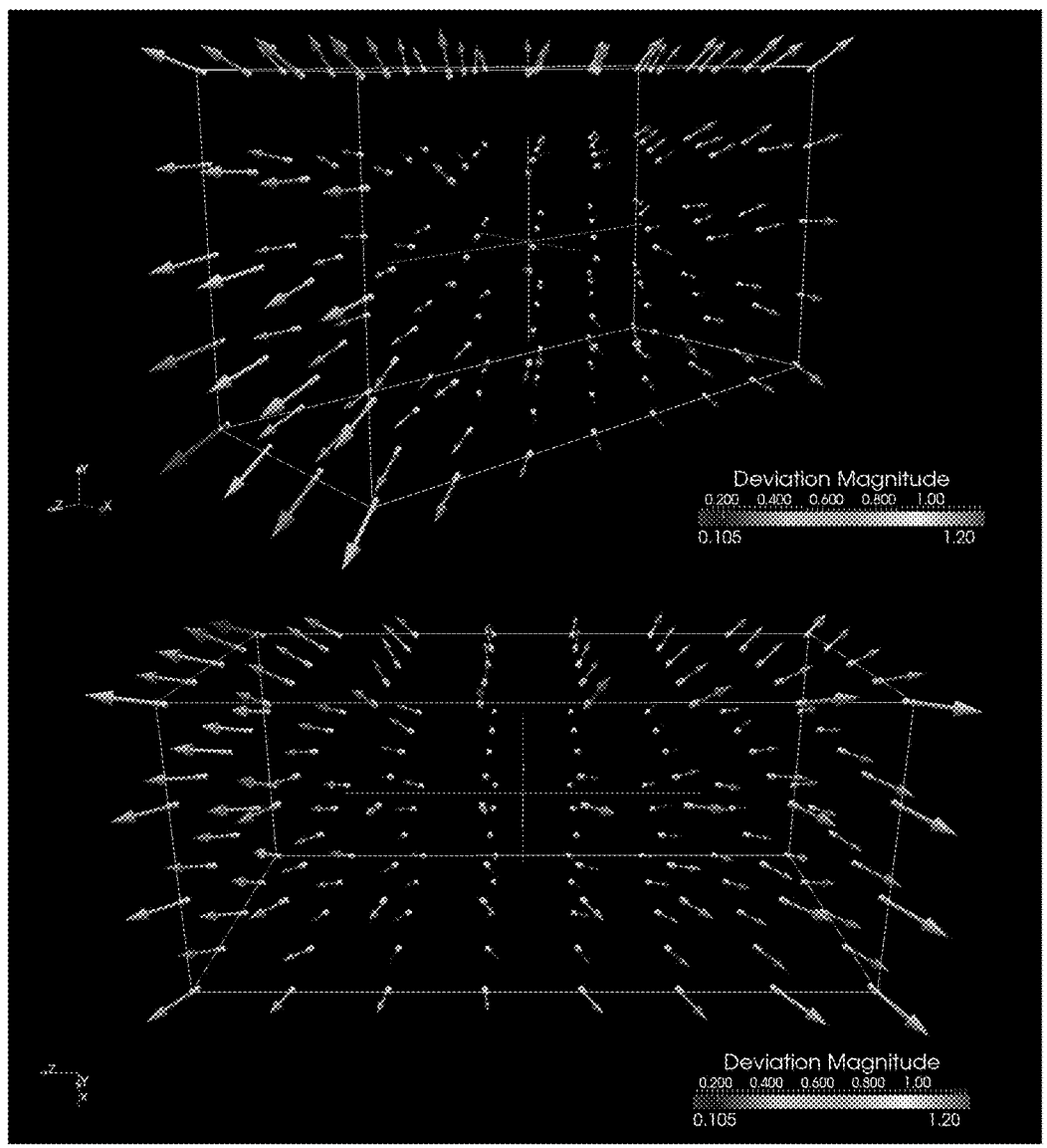

Referring to step 3.6, by comparing the location of the control points in the image with the actual or true ground location of the control points obtained by precise measurement of the phantom, a deviation between the image and the phantom may be observed. This deviation is used to obtain a spatial vector representative of the magnitude and direction of the deviation. The spatial vector represents the adjustment required to align the control points in the image with the actual control points in the phantom. Thus, the spatial vectors for each control point may be used to calibrate the imaging system or post-process the image to improve its accuracy. The spatial vectors may be represented for ease of interpretation on a vector map (as shown in FIG. 10) that relates the location of the points on the image to the true location of the points in the phantom.

The above methodology may be implemented using a calibration system or calibration kit comprising the phantom, optionally enclosed within the container, along with the measured locations of the control points and software or computer hardware configured to execute machine readable instructions for analyzing an acquired image. The instructions include the steps of identifying crisp boundaries of the image, eroding the boundaries, determining the centroid of the clusters and comparing those with the location of the control points in the phantom to arrive at a spatial vector for use in calibration and/or spatial mapping.

Further features and embodiments of the foregoing will be evident to persons of skill in the art. The inventor intends to cover all features, embodiments and sub-combinations thereof disclosed herein. The claims are to be construed as broadly as possible with reference to the specification as a whole. The invention may further be understood with reference to the following Examples.

EXAMPLES

[Component 1]

Figure 2:
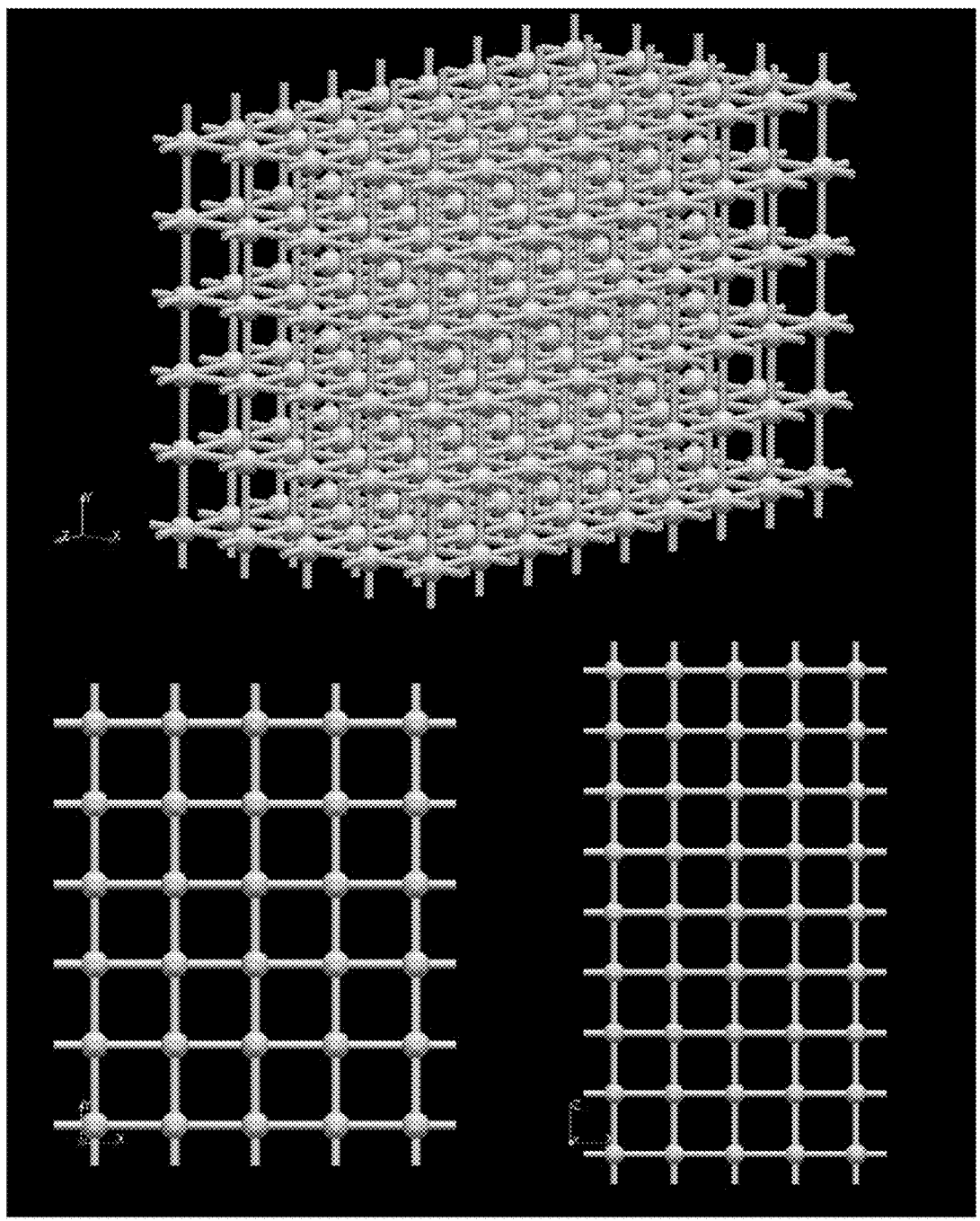
FIG. 2 is a computer-aided design (CAD) depiction of an embodiment of the phantom.
Figure 3:
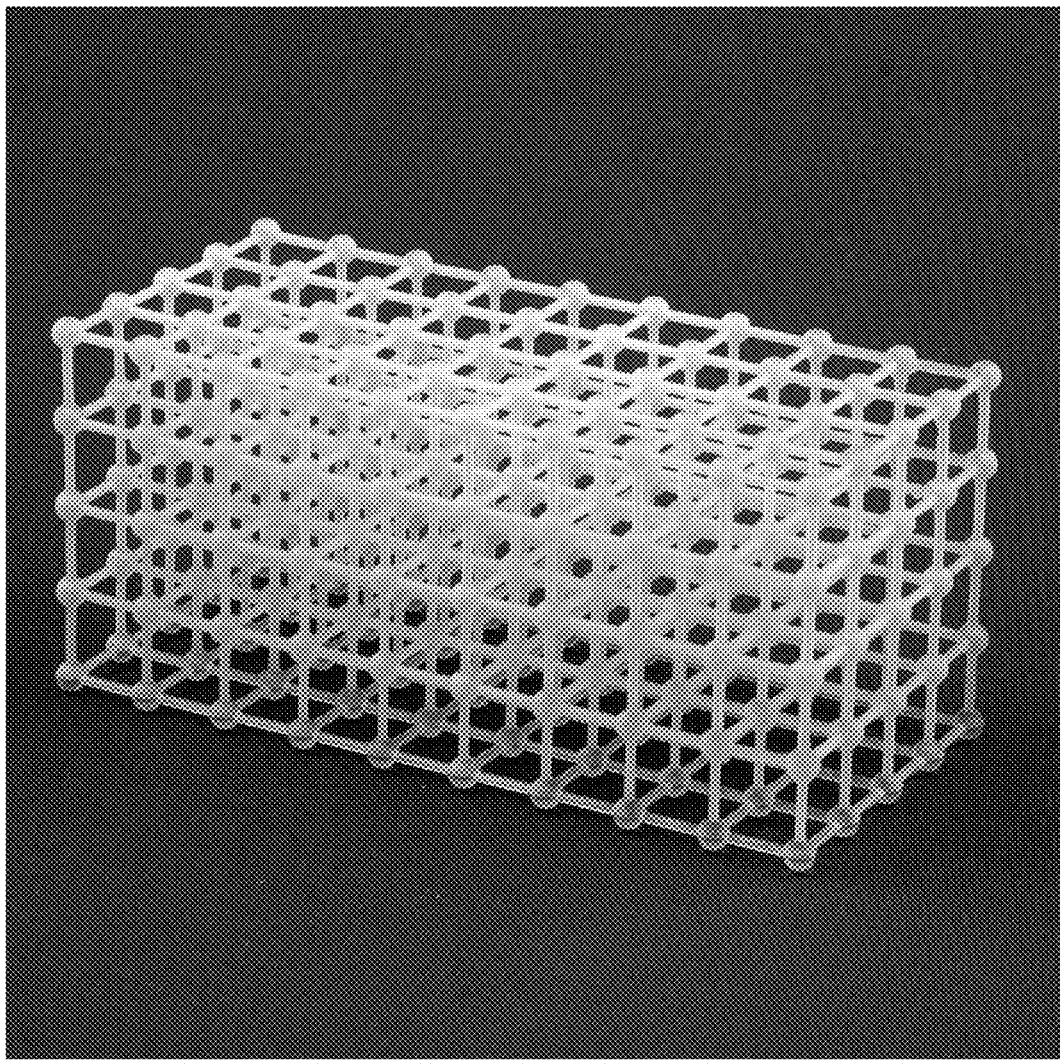
FIG. 3 is a photograph of the embodiment of FIG. 2, 3D printed in plastic resin.
Figure 4:
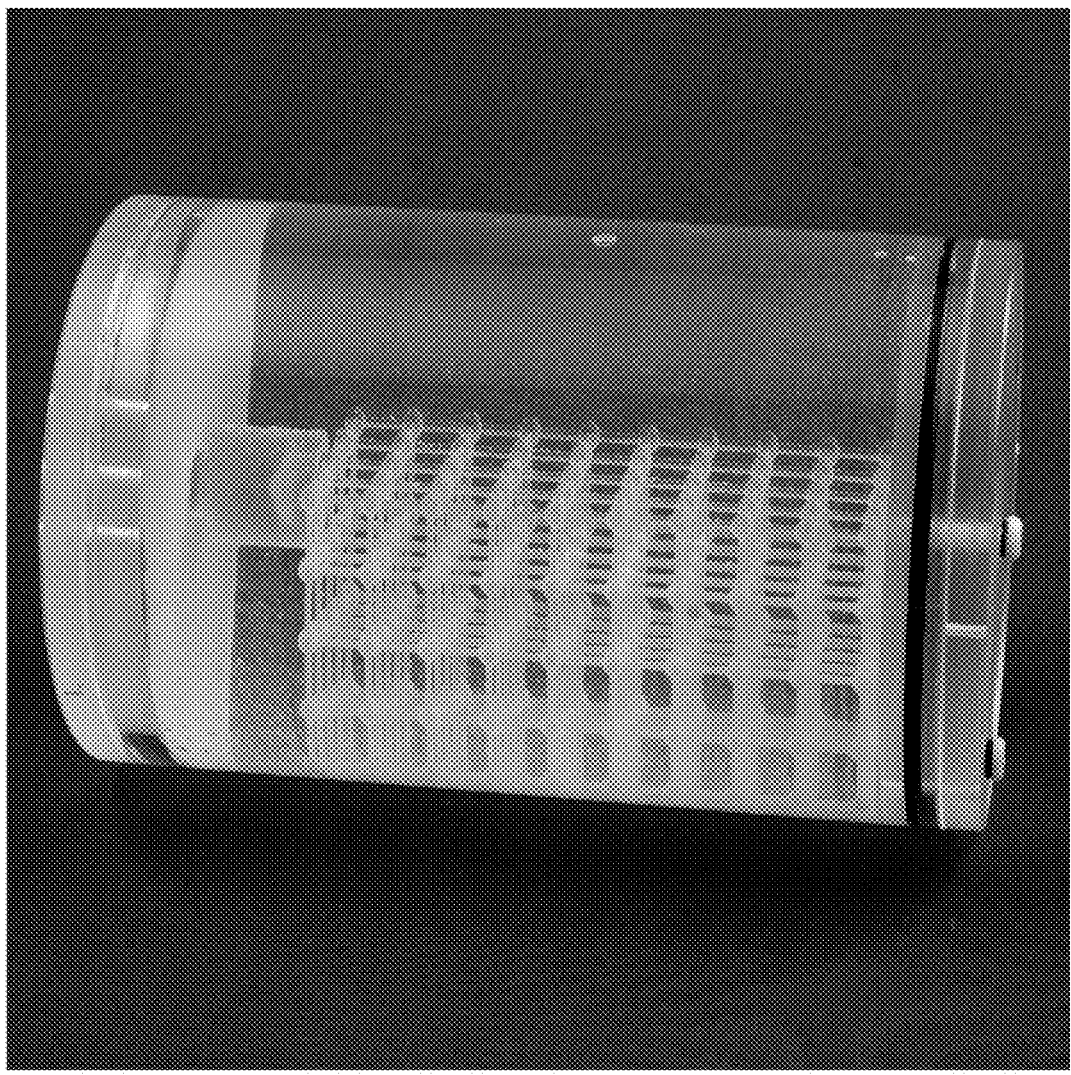
FIG. 4 is a photograph of the embodiment of FIG. 2 in a leak-tight container of paramagnetic liquid.

Referring to FIG. 2, the proposed distortion phantom is comprised of 4.5 mm diameter spheres, supported by 1.5 mm diameter cylindrical struts on nominal 13 mm spacing. A prototype version of this phantom is shown in FIG. 3, consisting of a 9×5×5 matrix, was fabricated using photopolymeric 3D printing (Objet 30 Pro, Stratasys™) with a transparent, rigid resin (VeroClear™, Stratasys™), with flexural modulus exceeding 2 GPa and water absorption of <1.5%. The 3D printer is designed to print over a 30×20×15 cm volume, with accuracy of ±0.1 mm. The fabricated plastic grid phantom was evaluated for geometric accuracy using a measuring microscope with accuracy of ±0.0005 mm (STM-6, Olympus™) and a micro-CT scanner (eXplore Ultra™, GE Healthcare). The measured control-point spacing was determined to be 13.079 mm, within ±0.6% of the nominal value. Micro-CT analysis showed that control-point centroids were within ±0.14 mm of their prescribed locations, on average. Referring to FIG. 4, after fabrication, the 3D plastic construct was immersed in a tissue-mimicking paramagnetic fluid to provide appropriate background signal, with T1<200 ms. A copper sulphate solution (7.8 mmol) in saline was used, following the description of Och et al. (Och 1992). The grid phantom exhibited a low volumetric packing fraction within the background liquid, displacing less than 5% of the imaging volume.

[Component 2]

Images were acquired at 3T (Discovery 750, GE Medical Systems) with a multi-channel knee coil, using a 3D turbo spin-echo sequence (CUBE, TR=2300 ms, TE=65 ms, flip angle=90°, 0.7 mm slice thickness, 0.7 mm in-plane resolution, 62.5 kHz readout bandwidth, matrix size 320×320× 160).

[Component 3]

Figure 5:
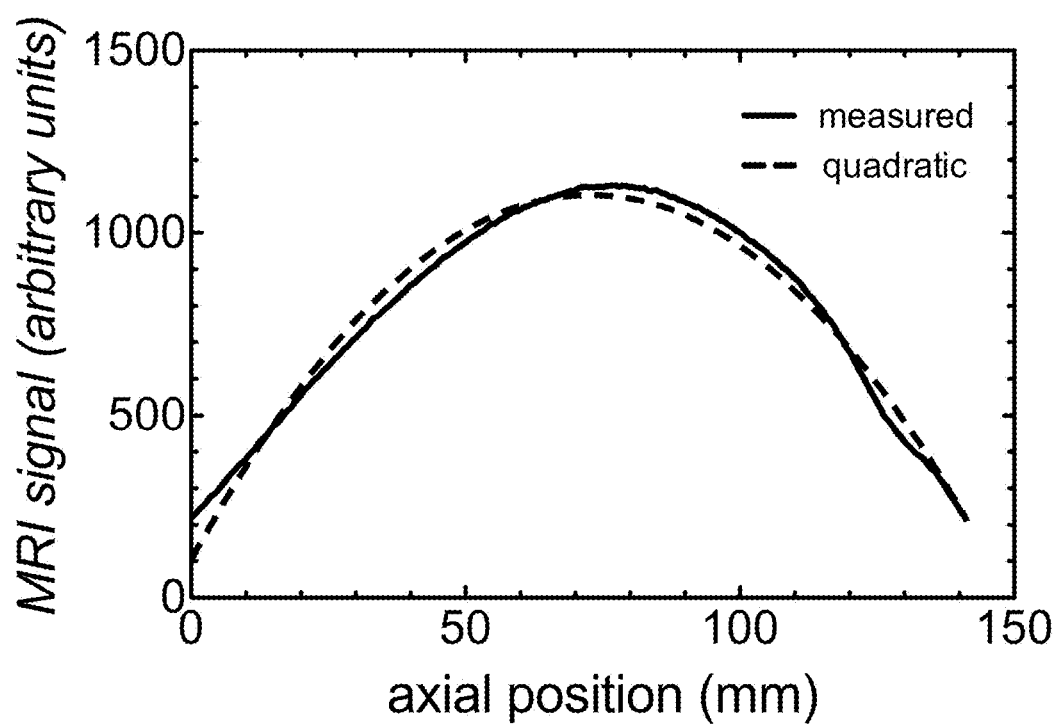
FIG. 5 is an illustration of an exemplary axial signal intensity profile of an MRI image, along with a fitted correction function.
Figure 6:
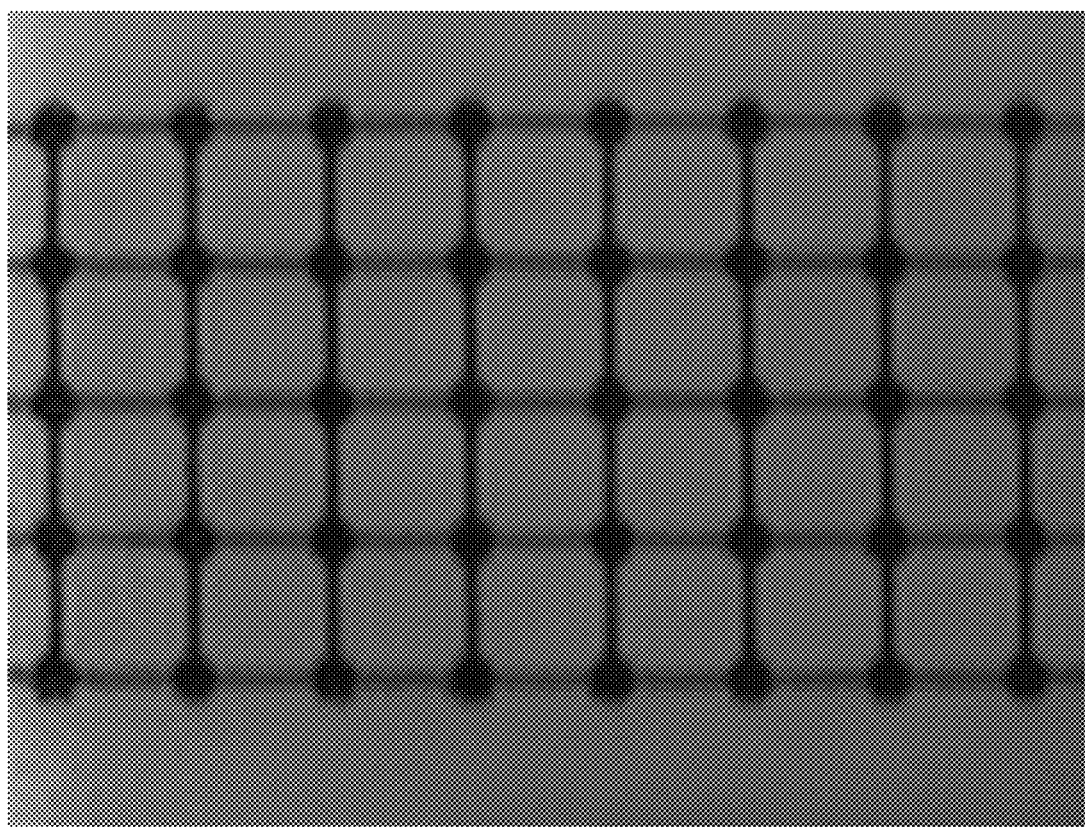
FIG. 6 is a MRI image taken through the central fiducial bead plane of the phantom of FIG. 2.
Figure 7:
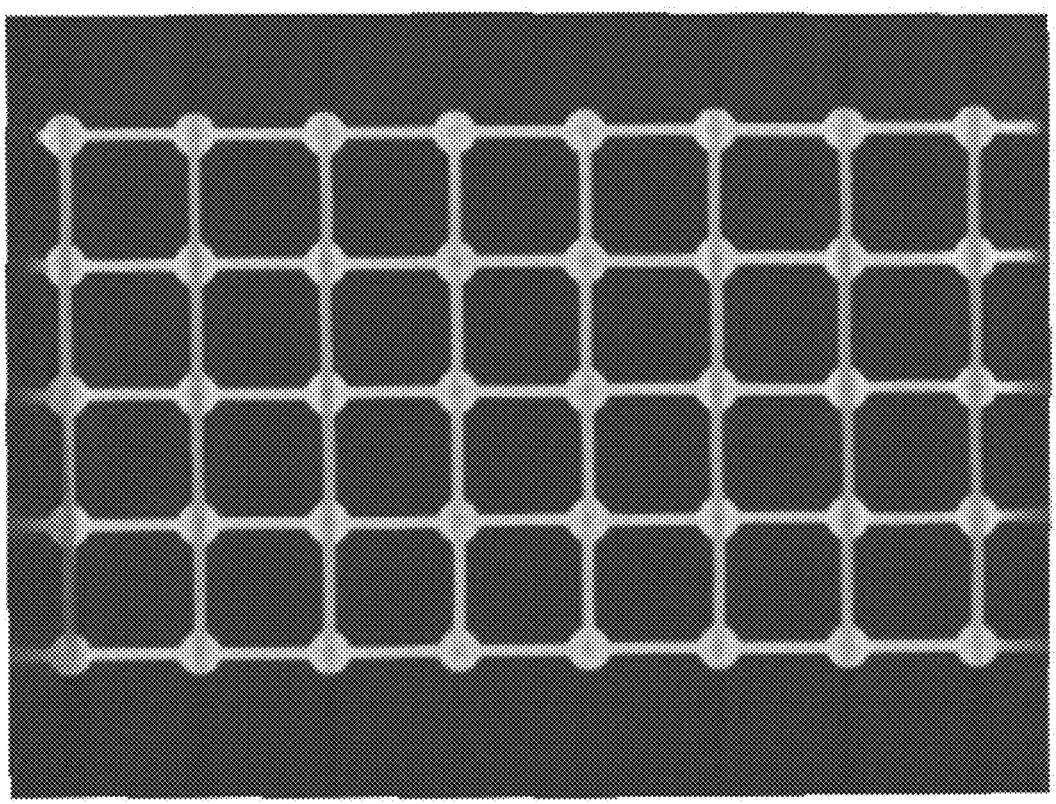
FIG. 7 is a CT image taken through the central fiducial bead plane of the phantom of FIG. 2.

To improve the accuracy of image segmentation, the resulting images were corrected for signal-intensity inhomogeneity in the axial and trans-axial directions, using fitted parabolic functions (FIG. 5). The resulting images of a dark grid on a bright background were interpolated to isotropic 0.43 mm resolution and segmented based on a grey-scale threshold (FIG. 6). Similar images were acquired with a micro-CT imaging system (eXplore Ultra™, GE Medical Systems) (FIG. 7).

[Component 3]

Figure 8:
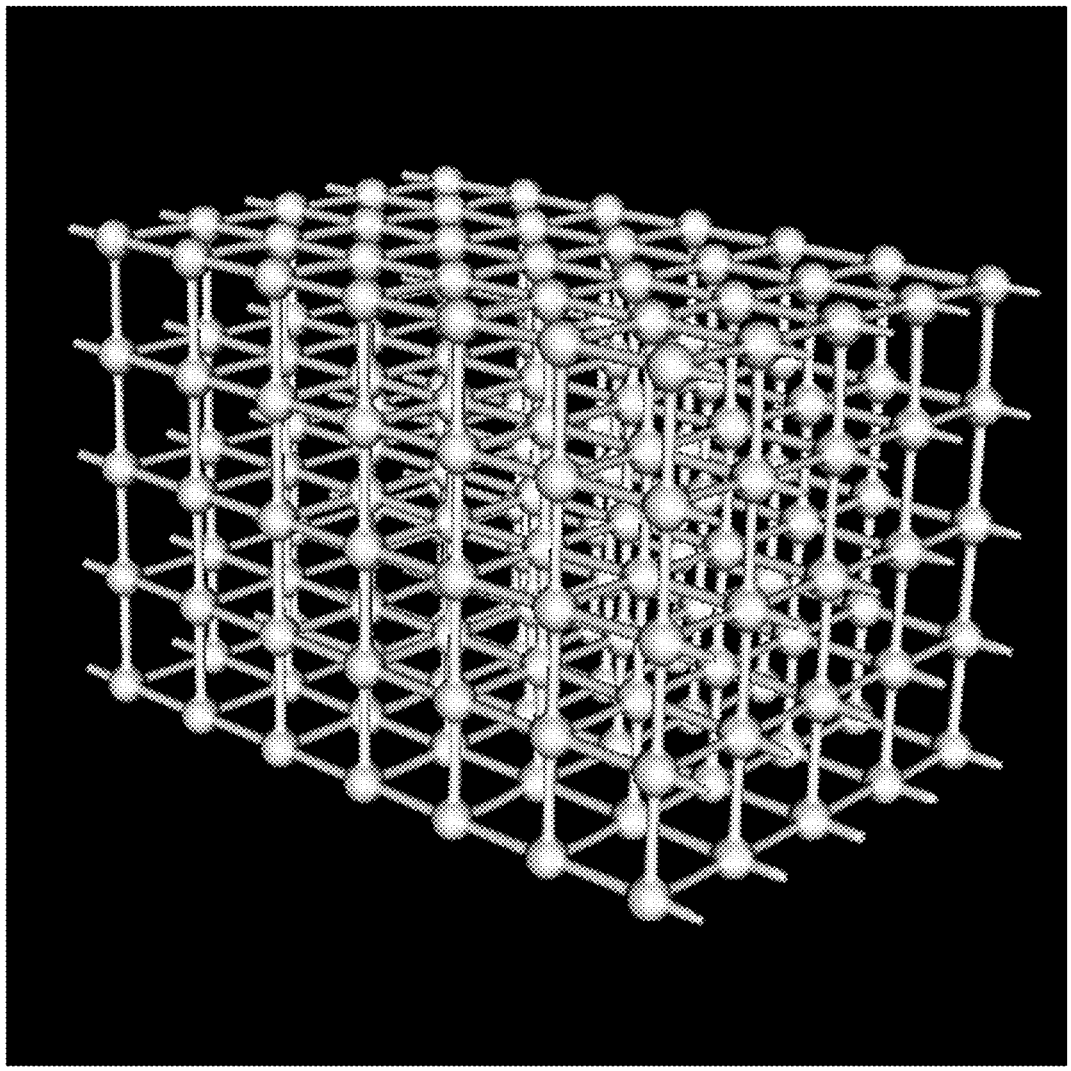
FIG. 8 is an isosurface of a segmented, binary volume image of the phantom of FIG. 2.
Figure 9:
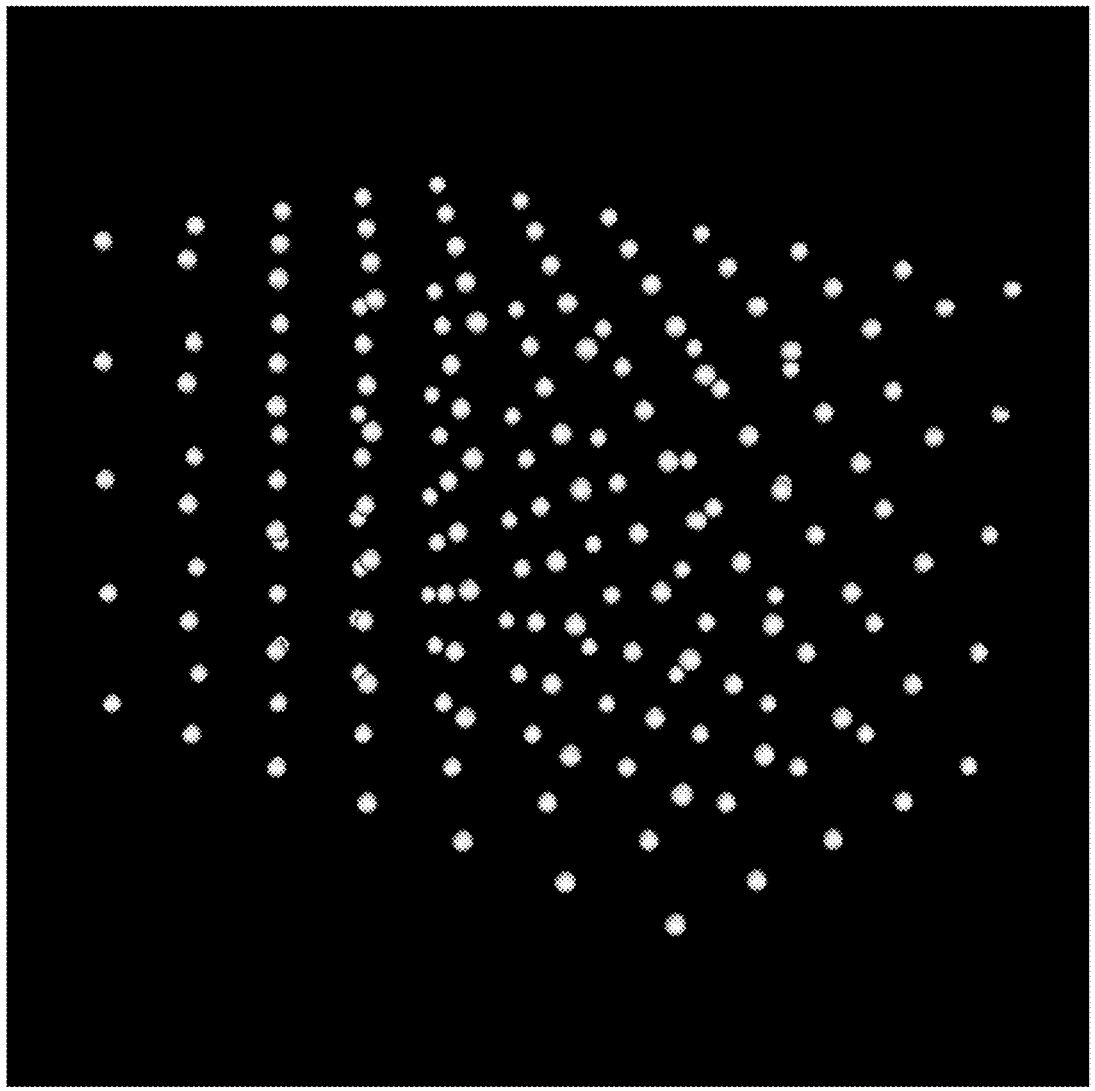
FIG. 9 is an isosurface of the isolated fiducial clusters after morphological erosion of the image of FIG. 8; and, FIG. 10 is geometric distortion vector map obtained from the image of FIG. 9.

To isolate individual fiducial locations within the grid, the segmented (binary) image (FIG. 8) was morphologically eroded to remove the struts, while retaining the beads at each intersection. In this case, erosion by a 3-pixel kernel removed 1.2 mm from every surface, thereby completely removing the struts and reducing the spheres to 2 mm diameter, as shown in FIG. 9. Each of the 175 spheres was then identified and centroided to create a 3D point cloud of observed grid locations. These measured locations were subsequently compared to the best-fit locations of a synthesized grid, based on the known grid spacing.

[Component 3]

FIG. 10 displays the produced 3D vector map of sub-voxel geometric deviation throughout the image volume. The derived geometric deviation map over the 11.7×6.5×6.5 cm3 volume showed average geometric deviations of 0.53 mm, ranging from 0.11 to 1.20 mm. The embodiment comprises a rigid and accurate phantom, which produces images that are amenable to fully automated quantitative analysis. This approach will be useful in any clinical application where geometric accuracy is important, either in routine quality assurance or as a component of distortion correction utilities.

REFERENCES

The contents of the entirety of each of which are incorporated by this reference.

U.S. Pat. No. 4,644,276 issued Feb. 17, 1987. Three-Dimensional Nuclear Magnetic Resonance Phantom.

U.S. Pat. No. 8,189,889 issued May 29, 2012. Systems and Methods for Characterizing Spatial Distortion in 3D Imaging Systems.

U.S. Pat. No. 5,005,578 issued Apr. 9, 1991. Three-Dimensional Magnetic Resonance Image Distortion Correction Method and System.

U.S. Pat. No. 5,872,829 issued Feb. 16, 1999. Method for the Detection and Correction of Image Distortions in Medical Imaging.

U.S. Pat. No. 7,330,026 issued Feb. 12, 2008. Method and Apparatus for Mapping and Correcting Geometric Distortion in MRI.

U.S. Pat. No. 7,535,227 issued May 19, 2009. Method and Apparatus for Correcting Distortion in MR Images Caused by Metallic Implants.

US Patent Publication 2009/0169083 published Jul. 2, 2009. Method and Device for Distortion Correction in Magnetic Resonance Imaging.

US Patent Publication 2012/0201438 published Aug. 9, 2012. Calibration Phantom and Method for Measuring and Correcting Geometric Distortions in Medical Images.

J. F. Aubry, J. Cheung, O. Morin, L. Beaulieu, I. C. Hsu, J. Pouliot. Investigation of geometric distortions on magnetic resonance and cone beam computed tomography images used for planning and verification of high-dose rate brachytherapy cervical cancer treatment. Brachytherapy. 9, 266-273 (2010).

L. N. Baldwin, K. Wachowicz, B. G. Fallone. A two-step scheme for distortion rectification of magnetic resonance images. Med Phys. 36, 3917-3926 (2009).

L. N. Baldwin, K. Wachowicz, S. D. Thomas, R. Rivest, B. G. Fallone. Characterization, prediction, and correction of geometric distortion in 3 T MR images. Med Phys. 34, 388-399 (2007).

Z. Chen, C. M. Ma, K. Paskalev, J. Li, J. Yang, T. Richardson, L. Palacio, X. Xu, L. Chen. Investigation of MR image distortion for radiotherapy treatment planning of prostate cancer. Phys Med Biol. 51, 1393-1403 (2006).

S. P. Crijns, C. J. Bakker, P. R. Seevinck, H. de Leeuw, J. J. Lagendijk, B. W. Raaymakers. Towards inherently distortion-free MR images for image-guided radiotherapy on an MRI accelerator. Phys Med Biol. 57, 1349-1358 (2012).

S. J. Doran, L. Charles-Edwards, S. A. Reinsberg, M. O. Leach. A complete distortion correction for MR images: I. Gradient warp correction. Phys Med Biol. 50, 1343-1361 (2005).

S. Kiryu, Y. Inoue, Y. Masutani, T. Haishi, K. Yoshikawa, M. Watanabe, K. Ohtomo. Distortion correction in whole-body imaging of live mice using a 1-Tesla compact magnetic resonance imaging system. Jpn J Radiol. 29, 353-360 (2011).

D. Kittle, B. Holshouser, J. M. Slater, B. D. Guenther, N. P. Pitsianis, R. D. Pearlstein. Technical note: rapid prototyping of 3D grid arrays for image guided therapy quality assurance. Med Phys. 35, 5708-5712 (2008).

S. P. Krishnan, et al. A review of rapid prototyped surgical guides for patient-specific total knee replacement. J Bone Joint Surg Br. 94(11), 1457-1461 (2012).

B. H. Kristensen, F. J. Laursen, V. Logager, P. F. Geertsen, A. Krarup-Hansen. Dosimetric and geometric evaluation of an open low-field magnetic resonance simulator for radiotherapy treatment planning of brain tumours. Radiother Oncol. 87, 100-109 (2008).

N. Maikusa, F. Yamashita, K. Tanaka, O. Abe, A. Kawaguchi, H. Kabasawa, S. Chiba, A. Kasahara, N. Kobayashi, T. Yuasa, N. Sato, H. Matsuda, T. Iwatsubo. Improved volumetric measurement of brain structure with a distortion correction procedure using an ADNI phantom. Med Phys. 40, 062303 (2013).

T. Mizowaki, Y. Nagata, K. Okajima, M. Kokubo, Y. Negoro, N. Araki, M. Hiraoka. Reproducibility of geometric distortion in magnetic resonance imaging based on phantom studies. Radiother Oncol. 57, 237-242 (2000).

J. G. Och, G. D. Clarke, W. T. Sobol, C. W. Rosen, S. K. Mun. Acceptance testing of magnetic resonance imaging systems: report of AAPM Nuclear Magnetic Resonance Task Group No. 6. Med Phys. 19, 217-229 (1992).

Y. Pauchard, M. R. Smith, M. P. Mintchev. Improving geometric accuracy in the presence of susceptibility difference artifacts produced by metallic implants in magnetic resonance imaging. IEEE Trans Med Imaging. 24, 1387-1399 (2005).

R. R. Price, L. Axel, T. Morgan, R. Newman, W. Perman, N. Schneiders, M. Selikson, M. Wood, S. R. Thomas. Quality assurance methods and phantoms for magnetic resonance imaging: report of AAPM nuclear magnetic resonance Task Group No. 1. Med Phys. 17, 287-295 (1990).

E. Schneider and M. Nessaiver, The Osteoarthritis Initiative (OAI) magnetic resonance imaging quality assurance update. Osteoarthritis Cartilage. 21(1), 110-116 (2013).

T. Stanescu, H. S. Jans, K. Wachowicz, B. G. Fallone. Investigation of a 3D system distortion correction method for MR images. J Appl Clin Med Phys. 11, 2961 (2010).

T. Stanescu, K. Wachowicz, D. A. Jaffray. Characterization of tissue magnetic susceptibility-induced distortions for MRIgRT. Med Phys. 39, 7185-7193 (2012).

S. F. Tanner, D. J. Finnigan, V. S. Khoo, P. Mayles, D. P. Dearnaley, M. O. Leach. Radiotherapy planning of the pelvis using distortion corrected MR images: the removal of system distortions. Phys Med Biol. 45, 2117-2132 (2000).

R. Viard, N. Betrouni, M. Vermandel, S. Mordon, J. Rousseau, M. Vanhoutte. Characterization and 3D correction of geometric distortion in low-field open-magnet MRI. Conf Proc IEEE Eng Med Biol Soc. 2008, 3649-3652 (2008).

D. Wang and D. M. Doddrell. A proposed scheme for comprehensive characterization of the measured geometric distortion in magnetic resonance imaging using a three-dimensional phantom. Med Phys. 31, 2212-2218 (2004a).

D. Wang, D. M. Doddrell, G. Cowin. A novel phantom and method for comprehensive 3-dimensional measurement and correction of geometric distortion in magnetic resonance imaging. Magn Reson Imaging. 22, 529-542 (2004b).

D. Wang, W. Strugnell, G. Cowin, D. M. Doddrell, R. Slaughter. Geometric distortion in clinical MRI systems Part II: correction using a 3D phantom. Magn Reson Imaging. 22, 1223-1232 (2004).

D. Wang, W. Strugnell, G. Cowin, D. M. Doddrell, R. Slaughter. Geometric distortion in clinical MRI systems Part I: evaluation using a 3D phantom. Magn Reson Imaging. 22, 1211-1221 (2004).

The novel features will become apparent to those of skill in the art upon examination of the description. It should be understood, however, that the scope of the claims should not be limited by the embodiments, but should be given the broadest interpretation consistent with the wording of the claims and the specification as a whole.

The invention claimed is:

1. A method that measures geometric distortions occurring in a 3D medical imaging that utilizes a 3D printed physical phantom that is immersible in a paramagnetic fluid, the method comprising:

a) providing the 3D printed physical phantom comprising a plurality of phantom control points imagable by using computed tomography (CT), or magnetic resonance imaging (MRI) when the 3D printed physical phantom has been immersed in the paramagnetic fluid, each phantom control point having a pre-determined location, with each phantom control point being supported on a supporting structure of the 3D printed physical phantom, where each phantom control point has a shape that is differentiable in a 3D image of the 3D printed physical phantom from the supporting structure that supports each of the control points in the 3D image of the 3D printed physical phantom;

b) obtaining the 3D image of the 3D printed physical phantom by using either magnetic resonance imaging (MRI) or computed tomography (CT);

c) identifying the phantom control points in the obtained 3D image of the 3D printed physical phantom by the use of both segmentation and morphological erosion, with the morphological erosion removing the supporting structure of each phantom control point from the obtained 3D image of the 3D printed physical phantom in order to leave image control points comprising isolated clusters of volume elements representing the phantom control points in the obtained 3D image of the 3D printed physical phantom;

d) determining with a computer a location of each of the image control points in the obtained 3D image of the 3D printed physical phantom;

e) comparing with the computer, the determined location of each of the image control points in the obtained 3D image of the 3D printed physical phantom with the pre-determined location of the phantom control points on the 3D printed physical phantom; and, f) from the comparison of step e, using the computer in order to derive a spatial vector for each image control point that quantifies geometric discrepancies between each of the 3D image control points and the pre-determined locations of the phantom control points located on in the 3D printed physical phantom.

2. The method according to claim 1, wherein the location of the image control points in the obtained 3D image of the 3D printed physical phantom is determined by having the computer perform the segmenting of the boundary of the 3D image of the 3D printed physical phantom using at least grey-scale threshold values, and then subsequently also performing morphological erosion of the boundary by removing a user specified number of boundary surface elements.

3. The method according to claim 1, wherein the location of the image control points in the obtained 3D image of the 3D printed physical phantom is determined by having the computer obtain a centroid with respect to each of the isolated clusters of volume elements.

4. The method according to claim 1, wherein the identification of each of the phantom control points is performed by and with the computer automatically.

5. The method according to claim 1, wherein the set of derived spatial vectors is a 3D vector map.

6. The method according to claim 1, wherein each phantom control point has a geometric cross-sectional size that is larger than a geometric cross-sectional size of the supporting structure on which each respective phantom control point is supported.

7. The method according to claim 1, wherein each of the phantom control points comprise spheres, each of the supporting structures comprise elongate members and the spheres have larger diameters than the diameter or width of the elongate members.

8. A system that measures geometric distortions occurring in a magnetic resonance (MR) or computed tomography (CT) 3D medical imaging system that utilizes a 3D printed physical phantom that is immersible in a paramagnetic fluid, comprising:

a) a 3D printed physical phantom immersible in a paramagnetic fluid when the phantom is used in the MR imaging system, the phantom comprising a plurality of phantom control points connected to each other by a supporting structure of the 3D printed physical phantom, the 3D printed physical phantom being suitable for imaging by the medical imaging system, the phantom control points each having a pre-determined location on the 3D printed physical phantom and a shape that is differentiable in a 3D image of the 3D printed physical phantom from the supporting structure whereby the use of morphological erosion removes the supporting structure from the 3D image of the 3D printed physical phantom and leaves image control points comprising isolated clusters of volume elements representing the phantom control points in the 3D image of the 3D printed physical phantom; and, b) a computer provided with non-transitory computer readable machine executable instructions that are configured to execute an analysis program that determines the location of at least one centroid with respect to each of the isolated clusters of volume elements in three-dimensional space from the 3D image of the 3D printed physical phantom and compares the locations of each of the centroids of the isolated clusters of volume elements to the pre-determined locations of the corresponding phantom control points on the 3D printed physical phantom, and calculates a spatial vector that relates to each centroid of the isolated clusters of volume elements to the predetermined location of the corresponding phantom control point on the 3D printed physical phantom.

9. The system according to claim 8, wherein each phantom control point has a geometric cross-sectional size that is larger than the geometric cross-sectional size of the supporting structure on which each respective phantom control point is supported.

10. The system according to claim 8, wherein each of the phantom control points comprise spheres, each of the supporting structures comprise elongate members and the spheres have larger diameters than the diameter or width of the elongate members.

11. The system according to claim 8, wherein each of the phantom control points are uniformly spaced apart.

12. The system according to claim 8, wherein the 3D printed physical phantom is provided within a leak-tight container that surrounds the 3D printed physical phantom and is able to contain the paramagnetic fluid.

13. The system according to claim 8, wherein the identification of the phantom control points in the 3D image is performed automatically by the computer.

14. The system according to claim 8, wherein the set of calculated spatial vectors is a 3D vector map.

15. A 3D printed physical phantom that is immersible in a paramagnetic fluid, the 3D printed physical phantom being configured for use in a system that measures geometric distortions occurring in a magnetic resonance (MR) or computed tomography (CT) 3D medical imaging system, the phantom comprising:

a plurality of phantom control points connected to each other by a supporting structure of the 3D printed physical phantom, the 3D printed physical phantom being suitable for imaging by the medical imaging system and immersible in a paramagnetic fluid when the 3D printed physical phantom is used in the MR imaging system, the phantom control points each having a pre-determined location on the 3D printed physical phantom and a shape that is differentiable in a 3D image of the 3D printed physical phantom produced by the medical imaging system from the supporting structure whereby the use of morphological erosion removes the supporting structure from the 3D image of the 3D printed physical phantom and leaves image control points comprising isolated clusters of volume elements representing the phantom control points in the 3D image of the 3D printed physical phantom produced by the medical imaging system; and wherein a computer provided with non-transitory computer readable machine executable instructions that is configured to execute an analysis program is able to:

1) determine at least one centroid of each of the isolated clusters of volume elements in three-dimensional space from the 3D image of the 3D printed physical phantom,
2) compare each of the centroids of the isolated cluster of volume elements to the pre-determined locations of the corresponding phantom control points of the 3D printed physical phantom, and
3) calculate a spatial vector that relates each centroid of the isolated clusters of volume elements to the pre-determined location of the corresponding phantom control point on the 3D printed physical phantom.

16. The 3D printed physical phantom, according to claim 15, wherein each phantom control point has a geometric cross-sectional size that is larger than the geometric cross-sectional size of the supporting structure on which each respective phantom control point is supported.

17. The 3D printed physical phantom, according to claim 15, wherein each of the phantom control points comprise spheres, each of the supporting structures comprise elongate members and the spheres have larger diameters than the diameter or width of the elongate members.

18. The 3D printed physical phantom, according to claim 15, wherein each of the phantom control points are uniformly spaced apart.

19. The 3D printed physical phantom, according to claim 15, wherein each of the phantom control points are non-uniformly spaced apart.

20. The 3D printed physical phantom, according to claim 15, wherein the 3D printed physical phantom is provided within a leak-tight container that surrounds the 3D printed physical phantom and is able to contain the paramagnetic fluid.

* * * * *